(12) United States Patent
Di Meo et al.

(10) Patent No.: US 8,063,003 B2
(45) Date of Patent: Nov. 22, 2011

(54) CYCLIC PHOSPHAZENE COMPOUND

(75) Inventors: Antonella Di Meo, Caronna Pertusella (IT); Rosaldo Picozzi, Cesate (IT)

(73) Assignee: Solvay Solexis S.p.A., Bollate (MI) (IT)

( * ) Notice: Subject to any disclaimer, the term of this patent is extended or adjusted under 35 U.S.C. 154(b) by 523 days.

(21) Appl. No.: 12/305,061

(22) PCT Filed: Jun. 22, 2007

(86) PCT No.: PCT/EP2007/056272
§ 371 (c)(1),
(2), (4) Date: Dec. 16, 2008

(87) PCT Pub. No.: WO2008/000706
PCT Pub. Date: Jan. 3, 2008

(65) Prior Publication Data
US 2009/0209442 A1    Aug. 20, 2009

(30) Foreign Application Priority Data

Jun. 29, 2006 (EP) .................................. 06116354

(51) Int. Cl.
*C10M 169/04* (2006.01)
*C10M 137/16* (2006.01)
*C07F 9/6581* (2006.01)
*C07F 9/659* (2006.01)
*C08G 79/02* (2006.01)

(52) U.S. Cl. ........................ 508/422; 508/424
(58) Field of Classification Search .................. 508/422, 508/424
See application file for complete search history.

(56) References Cited

U.S. PATENT DOCUMENTS

| | | | |
|---|---|---|---|
| 3,201,445 A | 8/1965 | Drysdale et al. | |
| 3,214,478 A | 10/1965 | Milian | |
| 3,242,218 A | 3/1966 | Miller | |
| 3,665,041 A | 5/1972 | Sianesi et al. | |
| 3,715,378 A | 2/1973 | Sianesi et al. | |
| 4,523,039 A | 6/1985 | Lagow et al. | |

FOREIGN PATENT DOCUMENTS

| | | |
|---|---|---|
| CA | 786877 A | 6/1968 |
| EP | 0148482 A2 | 7/1985 |
| EP | 0287892 A2 | 10/1988 |
| EP | 0597369 A1 | 5/1994 |
| EP | 1219629 A1 | 7/2002 |
| EP | 1336614 A1 | 8/2003 |
| GB | 1226566 A | 3/1971 |
| WO | W08700538 A1 | 1/1987 |

OTHER PUBLICATIONS

Maccone, P., et al. "New additives for fluorinated lubricants", 70th National Lubricating Grease Institute Annual Meeting, Hilton Head Island, South Carolina (Oct. 25-29, 2003). No.#318—11 pp.

*Primary Examiner* — Jim Goloboy
(74) *Attorney, Agent, or Firm* — Beatrice C. Ortego

(57) ABSTRACT

A cyclic phosphazene compound complying with formula (I) or (II):

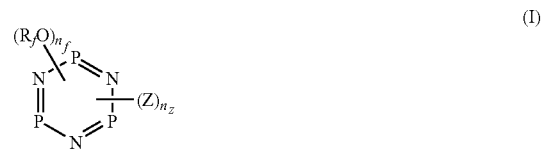

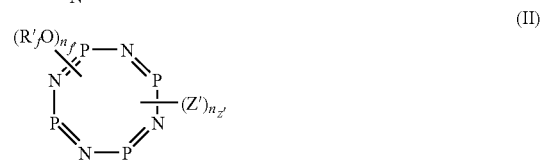

wherein:
$R_f$ and $R'_f$ represent independently a (per)fluoropolyoxyalkylene chain comprising recurring units $R°$, said recurring units, distributed randomly through the (per)fluoropolyoxyalkylene chain, being chosen among; (i) —CFXO—, X being F or $CF_3$; (ii) —$CF_2CFXO$—, X being F or $CF_3$; (iii) —$CF_2CF_2CF_2O$—; (iv) —$CF_2CF_2CF_2CF_2O$—;

Z and Z' represent a polar group of formula —$O^-M^+$, M being chosen among hydrogen, a monovalent metal, or an ammonium radical of formula $NR_1R_2R_3R_4$, or represent a polar group of formula —$O^-)_2M'^{2+}$, M' being a divalent metal;

$n_Z$ is an integer from 1 to 3;
$n_{Z'}$ is an integer from 1 to 4;
$n_f'$ is an integer such that $n_{Z'}+n_{f'}$ is equal to 8; and
$n_f$ is an integer such that $n_Z+n_f$ is equal to 6.

15 Claims, No Drawings

CYCLIC PHOSPHAZENE COMPOUND

CROSS-REFERENCE TO RELATED APPLICATIONS

This application is a U.S. national stage application under 35 U.S.C. §371 of International Application No PCT/EP2007/056272 filed Jun. 22, 2007, which claims priority to European Application No. 06116354.9, filed Jun. 29, 2006, these aplications being herein incorporated by reference in their entirety for all purposes.

TECHNICAL FIELD

The present invention relates to cyclic phosphazene compounds useful as anti-wear additives for lubricating oils and greases.

More specifically, the invention relates to cyclic phosphazenes having improved anti-wear properties combined with improved solubility/dispersibility in perfluoropolyethers oils and greases, to a process for their manufacture, to composition comprising the same and to the use of said cyclic phosphazenes or of the composition thereof as anti-wear additive in lubricants.

BACKGROUND ART

Lubricants are largely used in systems comprising moving mechanical parts for reducing the wear of said mechanical parts. Perfluoropolyethers have been well established in the lubrication industry in this application for over 30 years. Due to their chemical inertness, non flammability, excellent temperature-viscosity properties and high thermal and oxidative resistance, these fluids found application in specialized sectors requiring particularly severe conditions (temperature up to 300° C.) or extremely harsh environment, such as aerospace, military, oxygen and aggressive chemical handling, and the like.

Nevertheless, despite these outstanding properties of perfluoropolyethers, said perfluoropolyethers are not generally endowed with satisfactory anti-wear properties: these materials generally show wear values well above those generally obtained with hydrocarbon or synthetic oils and do not provide protection against corrosion due to their high permeability to gases and moisture.

Anti-wear additives generally employed in conventional hydrogenated lubricants cannot be used for these fluids, because of their poor solubility in perfluoropolyethers.

Thus,

Patent Citation 0001: U.S. Pat. No. 3,201,445 (E.I. DU PONT DE NEMOURS). Aug. 17, 1965. discloses cyclic phosphazenes bearing polyfluoroether alcohols moieties complying with formula here below:

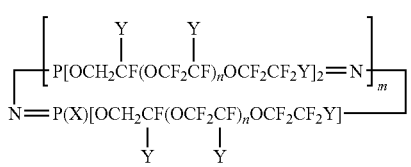

wherein:

X is a halogen atom or a group of formula:

Y is F or $CF_3$;
n is an integer of from 1 to 10; and
m is an integer from 2 to 3,
said compounds being suitable to be used as high temperature lubricants.

Patent Citation 0002: EP 0597369 A (AUSIMONT S.P.A.). Aug. 18, 1964. discloses fully substituted phosphazenes of cyclic or linear structure complying with formula here below:

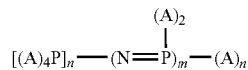

wherein:
n is 0 or 1;
m is an integer from 3 to 7;
groups A are selected from:
(i) R-Q-, in which Q is a divalent group selected from —O—, —S—, —$NR_1$—($R_1$=$C_{1-4}$ alkyl) and —NH—NH—; R is a $C_6$-$C_{12}$ aryl group;
(ii) $R_f$—$CH_2$—O($CH_2CH_2O$)$_s$—, in which s=0,1 and $R_f$ is a perfluoropolyethereal chain having molecular weight from 400 to 10 000, said compounds being used as stabilizers for oils and greases based on perfluoropolyethers.

Patent Citation 0003: EP 1219629 A (MATSURAMA OIL RESEARCH COMPANY). Jul. 3, 2002.
relates to a phosphazene compound complying with formula here below:

$$A\text{-}OCH_2CF_2O(CF_2CF_2O)_p(CF_2O)_qCF_2CH_2O\text{-}A$$

wherein A is a group of formula:

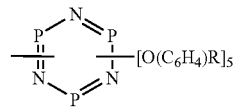

wherein R is a hydrogen atom, $C_{1-4}$ alkyl, $C_{1-4}$ alkoxy, haloalkyl, aryl, substantially aryl, aryloxy or substituted aryloxy, and p and q are a real number of 1 to 30, said compounds being useful to be used in lubricants for recording media such as hard disks or metal vapor-deposited tapes of video tape recorders or digital video cassettes.

Also, have been described in the past
(Patent Citation 0004: EP 0287892 A (HITACHI METALS). Oct. 26, 1988.) synthetic lubricants for magnetic media complying with formula (B) here below:

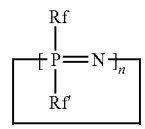

wherein n represents an integer of 3 to 10, and Rf and Rf' represent one or two groups selected from the following groups:

$Y(C_3F_6O)_l-CFYCH_2O-$ $Y(C_3F_6O)_l-(CF_2O)_m-CFYCH_2O-$ $Y(C_2F_4O)_l-(CF_2O)_m-CFYCH_2O-$ $Y(CF_2)_{1-1}-C_2H_4O-$ $Y(CF_2)_{1-1}-CH_2O-$ $H(CF_2)_{1-1}-CH_2O-$ where l represents 3 to 250, m 1 to 250, and Y one selected from the group consisting of $F-$, $CF_3-$, $C_2F_5-$, $CF_3O-$, $C_2F_5O-$ and $C_3F_7O-$. Said lubricating agents are endowed with improved adhesion properties to the surface of inorganic materials such as metal, carbon, ceramic, glass. These lubricants are not suggested to be used as anti-wear additives for oils and greases.

Moreover,

Patent Citation 0005: EP 1336614 A (SOLVAY SOLEXIS S.P.A.). Aug. 20, 2003. discloses cyclic phosphazene compounds comprising one or more cyclic moiety of formula:

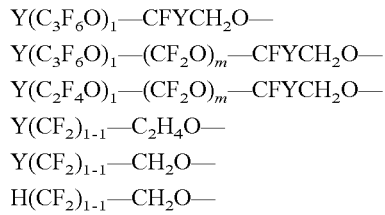

having bound to all the phosphorus atoms substituents comprising (per)fluoroalkyloxychains having a number averaged molecular weight in the range 280-5000 and end groups of the $-OCF_2X$, $-OC_2F_4X$, $-OC_3F_6X$ type, wherein X=F, Cl, H, wherein said cyclic phosphazenes are suitable for being used as additives for perfluoropolyether oils and greases.

Non Patent Citation 0001: MACCONE, P. New additives for fluorinated lubricants. 70th NLGI Annual Meeting, Hilton Head Island, S.C. (Oct. 25-29, 2003), no. #318.

discloses, inter alia, additives for fluorinated oils and greases complying with formula (A) here below:

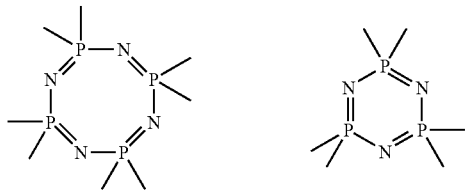

Nevertheless, the phosphazene compounds of the prior art, even if effective in reducing the wear and increasing upper operating temperature of perfluoropolyether oils and greases, possess a moderate solubility/dispersibility in said oils and greases, which can impair their anti-wear performances in corresponding admixture.

There is still a need in the art for antiwear and anticorrosion additives combining outstanding anti-wear properties to suitable solubility and/or dispersibility in perfluoropolyether oils and greases.

DISCLOSURE OF INVENTION

It is thus an object of the present invention to provide a cyclic phosphazene compound complying with formula (I) or (II) here below:

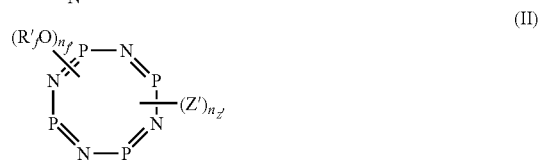

wherein:

$R_f$ and $R'_f$, equal or different each other and at each occurrence, represent independently, a (per)fluoropolyoxyalkylene chain [chain (OF)] comprising (preferably consisting essentially of) recurring units $R^o$, said recurring units, distributed randomly through the (per)fluoropolyoxyalkylene chain, being chosen among:

(i) $-CFXO-$, wherein X is F or $CF_3$, (ii) $-CF_2CFXO-$, wherein X is F or $CF_3$, (iii) $-CF_2CF_2CF_2O-$, (iv) $-CF_2CF_2CF_2CF_2O-$ Z and Z', equal or different each other and at each occurrence, represent a polar group of formula $-O^-M^+$, wherein M is chosen among hydrogen, a monovalent metal, preferably an alkaline metal selected from Li, Na, K, an ammonium radical of formula $NR_1R_2R_3R_4$, wherein each of $R_1$, $R_2$, $R_3$, $R_4$ is, independently, an hydrogen atom or a $C_1$-$C_{12}$ hydrocarbon group, optionally fluorinated, or a polar group of formula $-O^-)_2M'^{2+}$, wherein M' is a divalent metal, preferably an alkaline earth metal selected from Ca, and Mg [group (P)];

$n_Z$ is an integer from 1 to 3, preferably equal to 1;

$n_{Z'}$ is an integer from 1 to 4, preferably equal to 1;

$n_{f'}$ is an integer such that $n_{Z'}+n_{f'}$ is equal to 8;

$n_f$ is an integer such that $n_Z+n_f$ is equal to 6.

As per the expression "distributed randomly through the (per)fluoropolyoxyalkylene chain" it is understood that should the (per)fluoropolyoxyalkylene chain comprise recurring units of different types, said recurring units are statistically distributed along said chain.

The Applicant has surprisingly found that the cyclic phosphazene compound complying with formula (I) or (II) as above detailed, thanks to the presence of one or more than one group (P) as above described, possesses advantageously outstanding solubility/dispersibility in perfluoropolyether oil and greases, accompanied by excellent anti-wear properties.

The cyclic phosphazene compound of the invention can thus be advantageously employed as anti-wear additive in lubricants, e.g. in perfluoropolyether lubricants.

Other objects of the invention are a process for the manufacture of said cyclic phosphazene compound, a composition comprising the same and the use of said cyclic phosphazene compound or of the composition thereof as anti-wear additive in lubricants.

The chain (OF) has a number averaged molecular weight of advantageously at least 150, preferably at least 200, more preferably at least 250 and advantageously at most 10 000, preferably at most 7500, more preferably at most 5000.

Particularly good results have been obtained when the chain (OF) had a number averaged molecular weight of from 450 to 600.

Number averaged molecular weight of the chain (OF) can be advantageously determined by NMR.

Preferably, the cyclic phosphazene compound of the invention complies with formula (I) or (II) here above, wherein the groups $R_fO-$ and $R'_fO-$ are selected among:

    (a)

wherein:
- J is a group of formula $-CE'(Y)CE_2O(CH_2CH_2O)_{s1}-$ or $-CE'YO(CH_2CH_2O)_{s2}-$, wherein s1 and s2, equal or different each other and at each occurrence, are integers from 0 to 5, Y is F or $CF_3$ and E and E', equal or different each other and at each occurrence, are selected among F, H and $CF_3$, preferably E is H and E' is F or $CF_3$;
- T is selected from $-CF_3$, $-CF_2CF_3$, $-CF_2CF_2CF_3$, $-(CF_2)_f-CF_2(T_1)$, or $-(CF_2)_f-CF(T_1)(T_2)$, wherein f is 0 or 1, $T_1$ and $T_2$, equal or different each other, are at each occurrence independently chosen among Cl, Br and H;
- p' and q' are numbers such that p'+q' is in the range 1-100 and the q'/p' ratio is comprised between 0.1 and 10;

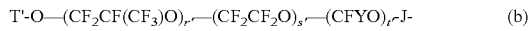    (b)

wherein:
- J has the same meaning as above described;
- T' is selected from $-CF_3$, $-CFY-CF_3$, $-CF(Y)CF(Y)CF_3$, $-(CFY)_f-CFY(T'_1)$, or $-(CFY)_f-CY(T'_1)(T'_2)$, wherein f is 0 or 1, $T'_1$ and $T'_2$, equal or different each other, are at each occurrence independently chosen among Cl, Br and H;
- Y is F or $CF_3$;
- r', s' and t' are numbers such that r'+s'+t' is in the range 1-100, the t'/(r'+s') ratio is comprised between 0.01 and 0.1;

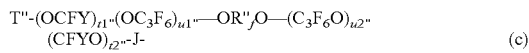    (c)

wherein:
- J has the same meaning as above described;
- $R''_f$ is a $C_1$-$C_8$ perfluoroalkylene;
- Y is F or $CF_3$;
- T'' is selected from $-CF_3$, $-CFY-CF_3$, $-CF(Y)CF(Y)CF_3$, $-(CFY)_f-CFY(T''_1)$, or $-(CFY)_f-CY(T''_1)(T''_2)$, wherein f is 0 or 1, $T''_1$ and $T''_2$, equal or different each other, are at each occurrence independently chosen among Cl, Br and H;
- t1'', u1'', t2'', u2'' are numbers such that (t1''+u1''+t2''+u2'') is in the range 1-100 and the (t1''+t2'')/(u1''+u2'') is comprised between 0.01 and 0.1;

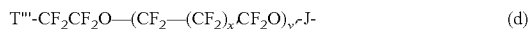    (d)

wherein:
- J has the same meaning as above described;
- T''' is selected from $-CF_3$, $-CF_2CF_3$, $-CF_2CF_2CF_3$, $-(CF_2)_f-CF_2(T'''_1)$, or $-(CF_2)_f-CF(T'''_1)(T'''_2)$, wherein f is 0 or 1, $T'''_1$ and $T'''_2$, equal or different each other, are at each occurrence independently chosen among Cl, Br and H;
- v' is a number in the range 1-100 and x' is 1 or 2;

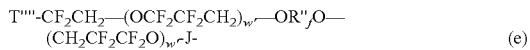    (e)

wherein:
- J has the same meaning as above described;
- $R''_f$ is as above;
- T'''' is selected from $-CF_3$, $-CF_2CF_3$, $-CF_2CF_2CF_3$, $-(CF_2)_f-CF_2(T''''_1)$, or $-(CF_2)_f-CF(T''''_1)(T''''_2)$, wherein f is 0 or 1, $T''''_1$ and $T''''_2$, equal or different each other, are at each occurrence independently chosen among Cl, Br and H;
- w'' is a number in the range 1-100.

More preferably, the cyclic phosphazene compound of the invention complies with formula (III) or (IV) here below:

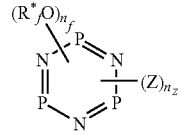    (III)

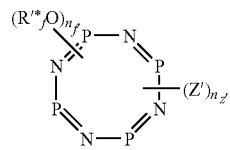    (IV)

wherein:
- Z, Z', $n_Z$, $n_Z'$, $n_f'$, $n_f$ have the same meaning as above defined;
- $R^*_fO-$ and $R^{*'}_fO-$ groups, equal or different each other and at each occurrence, represent independently, a (per)fluoropolyoxyalkylene chain of formula:

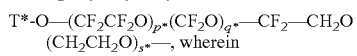, wherein

- s* in a number from 0 to 5;
- T* is selected from $-CF_3$, $-CF_2CF_3$, $-CF_2CF_2CF_3$;
- p* and q* are numbers such that p*+q* is in the range 1-50 and the q*/p* ratio is comprised between 0.1 and 10.

Particularly preferably, the cyclic phosphazene compound of the invention complies with formula (V) or (V-bis) here above:

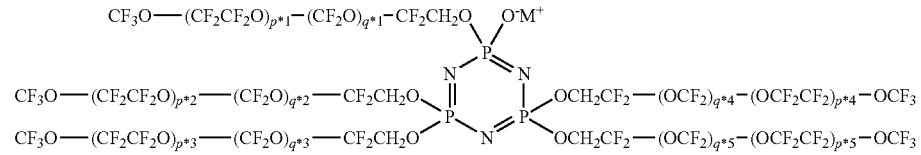    (V)

-continued

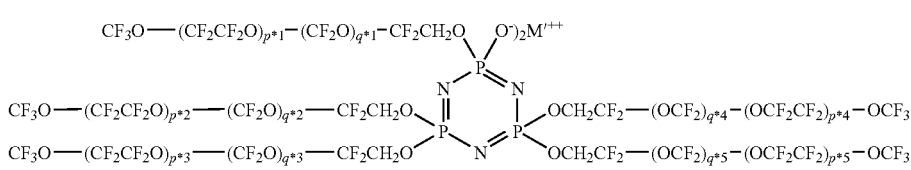

(V-bis)

wherein:
M and M' have the same meaning as above defined, preferably M is an alkaline metal selected from Li, Na, K or an ammonium radical of formula $NR_1R_2R_3R_4$, wherein each of $R_1$, $R_2$, $R_3$, $R_4$ is, independently, an hydrogen atom or a $C_1$-$C_{12}$ hydrocarbon group, preferably $R_1=R_2=R_3=R_4=$n-butyl, and preferably M' is an alkaline earth metal selected from Ca, Mg, more preferably M' is Ca;
each of $p*i$ (i=1 to 5) and $q*i$ (i=1 to 5) is independently an integer $\geq 0$ such that $p*i+q*i$ is in the range 2-25 and the $q*i/p*i$ ratio is comprised between 0.1 and 10.

A further object of the present invention is a process to prepare the cyclic phosphazene as above described.

The cyclic phosphazenes are advantageously prepared by a process comprising: (i) reaction, in the presence of a base, of a perhalophosphazene of formula (VI) or (VII):

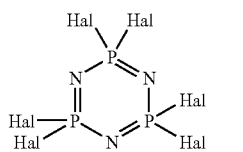

(VI)

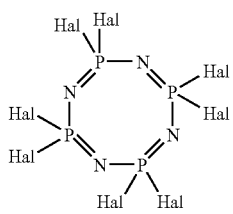

(VII)

wherein Hal represents an halogen chosen among fluorine, chlorine, bromine, iodine, preferably Hal is chlorine,
with a fluorinated alcohol of formula $R_fOH$, wherein $R_f$ has the meaning as above detailed to convert the P-Hal moieties in P—$OR_f$ moieties;
(ii) selective hydrolysis of at least one of the —P—$OR_f$ moieties per molecule to yield a —P—Z moiety, wherein Z has the meaning as above described, i.e. represent a polar group of formula —$O^-M^+$, wherein M is chosen among hydrogen, a monovalent metal, preferably an alkaline metal selected from Li, Na, K, an ammonium radical of formula $NR_1R_2R_3R_4$, wherein each of $R_1$, $R_2$, $R_3$, $R_4$ is, independently, an hydrogen atom or a $C_1$-$C_{12}$ hydrocarbon group, optionally fluorinated or a polar group of formula —$O^-)_2M'^{2+}$, wherein M' is a divalent metal, preferably an alkaline earth metal selected from Ca, and Mg.

Preferably the fluorinated alcohol complies with formula here below:

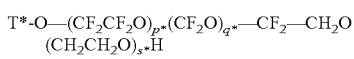

wherein:
s* in a number from 0 to 5;
T* is selected from —$CF_3$, —$CF_2CF_3$, —$CF_2CF_2CF_3$;
p* and q* are numbers such that p*+q* is in the range 1-50 and the q*/p* ratio is comprised between 0.1 and 10.

More specifically the process to obtain the cyclic phosphazene compound of the invention comprises the following steps:
(A) condensation reaction between a fluorinated alcohol as above described with the perhalophosphazene of formula (VI) or (VII) in an equivalent ratio alcohol/phosphazenes of at least about 1:1. This reaction can be carried out according to known methods, such as those described in EP 1 336 614 and EP 0 287 892.

Said reaction is generally carried out in one step, in an organic solvent, in the presence of a base and of a phase transfer agent.

Said reaction is typically carried out at a temperature in the range 20° C. to 120° C., preferably 40° C. to 100° C.

The organic solvent is selected from the known fluorinated or hydrofluorinated solvents well-known to the skilled in the art and having a boiling point generally in the range 20° C.-150° C. Suitable fluorinated solvents are notably perfluoropolyethers commercially available from Solvay Solexis under the trade name GALDEN®.

The amount of solvent is chosen such as for maintaining a ratio by weight solvent/fluorinated alcohol advantageously in the range 0.5-10, preferably 2-5.

As a base it is typically used an aqueous solution/dispersion of MOH (wherein M is chosen among hydrogen, a monovalent metal, preferably an alkaline metal selected from Li, Na, K, an ammonium radical of formula $NR_1R_2R_3R_4$, wherein each of $R_1$, $R_2$, $R_3$, $R_4$ is, independently, an hydrogen atom or a $C_1$-$C_{12}$ hydrocarbon group, optionally fluorinated) or of $M'(OH)_2$ (wherein M' is a divalent metal, preferably an alkaline earth metal selected from Ca, and Mg), preferably of KOH, NaOH or $Ca(OH)_2$, said aqueous solution/dispersion having a concentration comprised advantageously between 20% and 60% w/w, preferably between 30% and 50% w/w, in amounts to have a MOH or $M'(OH)_2$ molar excess comprised advantageously between 2 and 10 times the fluorinated alcohol.

The expression "solution/dispersion" is intended to denote aqueous composition of the base, as above detailed, wherein said base can be totally or partially solubilized or can be suspended with no or no significant dissolution.

The phase transfer agent is preferably a phosphonium salt or a quaternary ammonium salt well known to those skilled in the art; tetrabutylammonium hydroxide, tetramethylammonium chloride can be notably used.

Said phase transfer agent is used in a molar concentration comprised advantageously between 1% and 10% the fluorinated alcohol.

Depending on the temperature, reaction times are generally comprised between 4 and 24 hours.

At the end of the condensation reaction, two phases are generally formed. Optionally, an organic solvent at least partially miscible with water can be added for advantageously affecting phases separation. Preferably, aliphatic alcohols are used, like notably methanol, ethanol, isopropanol, isobutanol. Said phases are allowed to separate and the heavy organic phase is recovered.

The heavy organic phase obtained as above described is generally repeatedly washed with water to remove the phase transfer agent and the inorganic salts which can be generated during the reaction. The obtained product wherein the —P-Hal moieties have been converted in P—OR$_f$ moieties is then advantageously separated from the solvent by known methods, for example by evaporation and/or fractional distillation at reduced pressure.

(B) hydrolysis of the compound obtained in step (A) by treatment with a base in an alcoholic medium.

As base, use can be made of MOH or of M'(OH)$_2$, or of M'CO$_3$, wherein M and M' have the same meaning as above described; preferred base are KOH, Ca(OH)$_2$ and/or NaOH. The amount of base is generally chosen as a function of the targeted hydrolysis conversion required.

The hydrolysis is advantageously monitored by $^{31}$P-NMR, in order to obtain the required conversion of —P—OR$_f$ moieties in —P—Z groups, as above detailed.

The hydrolysis medium is alcoholic, that is to say it comprises at least one alcohol. Suitable alcohols are notably ethanol, methanol, isopropanol. The alcohol(s) can be used alone or in combination with a non-alcoholic solvent; for instance, mixtures of alcohol(s) and water can be advantageously employed.

The hydrolysis reaction is carried out at a temperature of at least 20° C., preferably at least 30° C., more preferably of at least 40° C. and advantageously at most 120° C., preferably at most 100° C. A range of temperatures which has been found particularly suitable for the controlled hydrolysis is that comprised between 60 and 80° C.

At the end of the hydrolysis reaction, two phases are generally formed; said phases are allowed to separate and the heavy organic phase is recovered.

The heavy organic phase obtained as above described is generally repeatedly washed with water to remove the base and the inorganic salts which can be generated during the reaction. The obtained product wherein at least one of the —P—OR$_f$ moieties per molecule has been converted in a —P—Z group is then advantageously separated from the solvent by known methods, for example by evaporation and/or fractional distillation at reduced pressure.

Should the cyclic phosphazene compound comprise a group Z of formula of formula —O$^-$)$_2$M'$^{2+}$, wherein M' is a divalent metal, preferably an alkaline earth metal selected from Ca, and Mg, it is possible to manufacture said product by:

preparing the corresponding cyclic phosphazene compound comprising a group Z of formula of formula —O$^-$M$^+$, wherein M is chosen among hydrogen, a monovalent metal, preferably an alkaline metal selected from Li, Na, K, an ammonium radical of formula NR$_1$R$_2$R$_3$R$_4$, wherein each of R$_1$, R$_2$, R$_3$, R$_4$ is, independently, an hydrogen atom or a C$_1$-C$_{12}$ hydrocarbon group, optionally fluorinated, as above described;

submitting said latter compound to hydrolysis, generally in the presence of an aqueous or aqueous alcoholic acid solution, so as to obtain the corresponding derivative comprising a group of formula —OH, and then treating said derivative with a base of formula M'(OH)$_2$ or M'CO$_3$, preferably M'(OH)$_2$, with M' being a divalent metal, preferably an alkaline-earth metal selected from Ca and Mg, more preferably Ca.

Still another object of the invention is a composition comprising the cyclic phosphazene compound as above described.

According to a first embodiment of the invention, the composition of the invention can comprise another cyclic phosphazene compound free from polar group of type Z and Z' as above described (phosphazene (NP)).

The Applicant thinks, without this limiting the scope of its invention, that in said composition the cyclic phosphazene of the invention, thanks to its surfactant-type properties conferred by the polar group, can advantageously promote the dispersion of the phosphazene (NP) in a suitable lubricant, thus maximizing the anti-wear properties of the phosphazene (NP).

As example of phosphazene (NP) which can be used in the composition according to the first embodiment of the invention, mention can be notably made of compounds such as those described in EP 1 336 614 and EP 0 287 892.

The phosphazene (NP) advantageously comply with formula (VIII) to (X) here below:

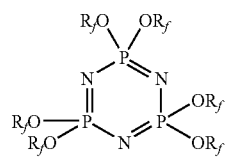

(VIII)

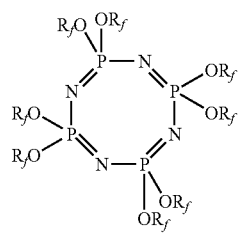

(IX)

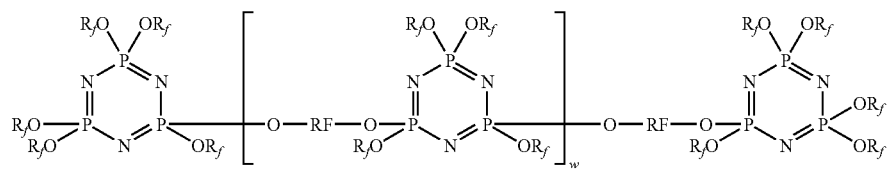

(X)

wherein $R_f$ has the meaning as above defined, w is an integer equal to 0 or 1, preferably w is 0, RF is a divalent group comprising (preferably consisting essentially of) recurring units $R°$, said recurring units, distributed randomly, being chosen among:
(i) —CFXO—, wherein X is F or $CF_3$,
(ii) —$CF_2$CFXO—, wherein X is F or $CF_3$,
(iii) —$CF_2CF_2CF_2O$—,
(iv) —$CF_2CF_2CF_2CF_2O$—.

According to a second embodiment of the invention, the composition of the invention comprises at least one lubricant.

Preferably, the composition according to the second embodiment of the invention comprises at least one (i.e. one or a mixture of more than one) perfluoropolyether (PFPE) lubricant, i.e. a lubricant comprising a perfluorooxyalkylene chain, that is to say a chain comprising recurring units having at least one ether bond and at least one fluorocarbon moiety.

PFPE lubricants can be classified in oils and greases; it is generally understood that oils are compounds having kinematic viscosity (ASTM D445) at 20° C. of from 30 to 30 000 cSt; greases are derived from such oils by addition of suitable thickeners, such as notably polytetrafluoroethylene (PTFE) or inorganic compounds, e.g. talc.

More preferably, the composition according to the second embodiment of the invention comprises a lubricant comprising at least one oil selected from the following groups:

$$B-O-[CF(CF_3)CF_2O]_{b1'}(CFXO)_{b2'}-B' \qquad (1)$$

wherein:
X is equal to —F or —$CF_3$;
B and B', equal to or different from each other, are selected from —$CF_3$, —$C_2F_5$ or —$C_3F_7$;
b1' and b2', equal to or different from each other, are independently integers ≧0 selected such that the b1'/b2' ratio is comprised between 20 and 1,000 and b1'+b2' is in the range 5 to 250; should b1' and b2' be both different from zero, the different recurring units are generally statistically distributed along the chain.

Said products can be obtained by photooxidation of the hexafluoropropylene as described in
Patent Citation 0006: CA 786877 (MONTEDISON S.P.A.). Apr. 6, 1968. and by subsequent conversion of the end groups as described in
Patent Citation 0007: GB 1226566 (MONTECATINI EDISON S.P.A.). Mar. 31, 1971.

$$C_3F_7O-[CF(CF_3)CF_2O]_{o'}-D \qquad (2)$$

wherein
D is equal to —$C_2F_5$ or —$C_3F_7$;
o' is an integer from 5 to 250.

Said products can be prepared by ionic hexafluoropropylene epoxide oligomerization and subsequent treatment with fluorine as described in
Patent Citation 0008: U.S. Pat. No. 3,242,218 (DU PONT). Mar. 22, 1966.

$$\{C_3F_7O-[CF(CF_3)CF_2O]_{dd'}-CF(CF_3)-\}_2 \qquad (3)$$

wherein
dd' is an integer between 2 and 250.

Said products can be obtained by ionic telomerization of the hexafluoropropylene epoxide and subsequent photochemical dimerization as reported in
Patent Citation 0009: U.S. Pat. No. 3,214,478 (DU PONT). Oct. 26, 1965.

$$C'-O-[CF(CF_3)CF_2O]_{c1'}(C_2F_4O)_{c2'}(CFX)_{c3'}-C'' \qquad (4)$$

wherein
X is equal to —F or —$CF_3$;
C' and C'', equal to or different from each other, are selected from —$CF_3$, —$C_2F_5$ or —$C_3F_7$;
c1', c2' and c3' equal or different from each other, are independently integers ≧0, such that and c1'+c2'+c3' is in the range 5 to 250; should at least two of c1', c2' and c3' be different from zero, the different recurring units are generally statistically distributed along the chain.

Said products can be manufactured by photooxidation of a mixture of $C_3F_6$ and $C_2F_4$ and subsequent treatment with fluorine as described in
Patent Citation 0010: U.S. Pat. No. 3,665,041 (MONTEDISON SPA). May 23, 1972.

$$D-O-(C_2F_4O)_{d1'}(CF_2O)_{d2'}-D' \qquad (5)$$

wherein
D and D', equal to or different from each other, are selected from —$CF_3$, —$C_2F_5$ or —$C_3F_7$;
d1' and d2' equal or different from each other, are independently integers ≧0, such that the d1'/d2' ratio is comprised between 0.1 and 5 and d1'+d2' is in the range 5 to 250; should d1' and d2' be both different from zero, the different recurring units are generally statistically distributed along the chain.

Said products can be produced by photooxidation of $C_2F_4$ as reported in
Patent Citation 0011: U.S. Pat. No. 3,715,378 (MONTEDISON SPA). Feb. 6, 1973.
and subsequent treatment with fluorine as described in
Patent Citation 0012: U.S. Pat. No. 3,665,041 (MONTEDISON SPA). May 23, 1972.

$$G-O-(CF_2CF_2C(Hal')_2O)_{g1'}-(CF_2CF_2CH_2O)_{g2'}-(CF_2CF_2CH(Hal')O)_{g3'}-G' \qquad (6)$$

wherein
G and G', equal to or different from each other, are selected from —$CF_3$, —$C_2F_5$ or —$C_3F_7$;
Hal', equal or different at each occurrence, is a halogen chosen among F and Cl, preferably F;
g1', g2', and g3' equal or different from each other, are independently integers ≧0, such that g1'+g2'+g3' is in the range 5 to 250; should at least two of g1', g2' and g3' be different from zero, the different recurring units are generally statistically distributed along the chain.

Said products may be prepared by ring-opening polymerizing 2,2,3,3-tetrafluorooxethane in the presence of a polymerization initiator to give a polyether comprising repeating units of the formula: —$CH_2CF_2CF_2O$—, and optionally fluorinating and/or chlorinating said polyether, as detailed in
Patent Citation 0013: EP 148482 A (DAIKIN INDUSTRIES). Jul. 17, 1985.

$$L-O-(CF_2CF_2O)_{l'}-L' \qquad (7)$$

wherein
L and L', equal to or different from each other, are selected from —$C_2F_5$ or —$C_3F_7$;
l' is an integer in the range 5 to 250.

Said products can be obtained by a method comprising fluorinating a polyethyleneoxide, e.g. with elemental fluorine, and optionally thermally fragmentating the so-obtained fluorinated polyethyleneoxide as reported in
Patent Citation 0014: U.S. Pat. No. 4,523,039 (THE UNIVERSITY OF TEXAS). Jun. 11, 1985.

$$R^1_f - \{C(CF_3)_2 - O - [C(R^2_f)_2]_{kk1} \cdot C(R^2_f)_2 - O\}_{kk2'} - R^1_f \qquad (8)$$

wherein
$R^1_f$ is a perfluoroalkyl group having from 1 to 6 carbon atoms;
$R^2_f$ is equal to —F or perfluoroalkyl group having from 1 to 6 carbon atoms;
kk1' is an integer from 1 to 2;
kk2' represents a number in the range 5 to 250.

Said products can be produced by the copolymerization of hexafluoroacetone with an oxygen-containing cyclic comonomer selected from ethylene oxide, propylene oxide, epoxy-butane and/or trimethylene oxide (oxethane) or substituted derivatives thereof and subsequent perfluorination of the resulting copolymer, as detailed in patent application
Patent Citation 0015: WO WO 87/00538 (LAGOW ET AL.). Jan. 29, 1987.

Preferred lubricants suitable for the purposes of the invention are notably:

those commercially available under the trade name FOMBLIN® (type Y, M, W, or Z) from Solvay Solexis, S.p.A.; lubricants of this family generally comprise at least one oil (i.e. only one or mixture of more than one oil) complying with either of formulae here below:

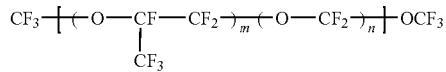

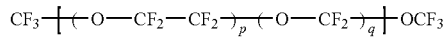

m + n = 8 - 45; m/n = 20 - 10 000
p + q = 40 - 180; p/q = 0,1 - 10 those commercially available under the trade name KRYTOX® from Du Pont de Nemours, said lubricants generally comprising at least one (i.e. one or mixtures of more than one) low-molecular weight, fluorine end-capped, homopolymer of hexafluoropropylene epoxide with the following chemical structure:

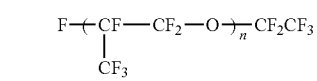

n = 10 to 60 those commercially available under the trade name DEMNUM® from Daikin, said lubricants generally comprising at least one (i.e. one or mixture of more than one) oil complying with formula:

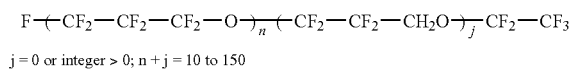

j = 0 or integer > 0; n + j = 10 to 150

More preferred lubricants are those commercially available under the trade name FOMBLIN®, as above detailed.

Still another object of the invention is the use of said cyclic phosphazene compound or of the composition thereof as anti-wear additive in lubricants.

Lubricants wherein the cyclic phosphazene compound or composition thereof can be used are those detailed hereinabove.

The invention will be now described in more detail with reference to the following examples, whose purpose is merely illustrative and not limitative of the scope of the invention.

EXAMPLE 1

Synthesis of a Hexasubstituted Phosphazene (Used as Hydrolysis Precursor)

1160 g (2.15 equivalents) of a fluorinated alcohol complying with formula: $T^{\#}O(CF_2CF_2O)_{p\#}(CF_2O)_{q\#}$—$CF_2$—$CH_2OH$, wherein $T^{\#}=CF_3$, and $p^{\#}$ and $q^{\#}$ are chosen such that the number averaged molecular weight of said alcohol is 539, 43.2 g of an aqueous solution at 40% by weight of $Bu_4N^+$ $OH^-$, 2900 g of GALDEN® HT110 as solvent and 125 g of perchlorocyclotriphosphazene (2.15 equivalents) were introduced in a 10 litres glass reactor equipped with mechanical stirrer, thermometer and a reflux condenser. 2020 g of an aqueous solution of KOH at 30% by weight were then introduced under vigorous stirring. The reaction mixture was heated at 60° C. and kept under stirring for about 6 hours. After cooling 260 g of isobutyl alcohol and 1400 g of water were added and the resulting mixture was stirred for 30 minutes. The phases were then allowed to separate and the heavy organic phase was recovered and washed with 500 g of methyl alcohol. After the heavier organic phase separation the solvent was distilled and the product stripped at 100° C. for 1 hour. 1112 g of product were obtained with a yield of 92%. The IR and NMR analyses ($^{31}P$, $^1H$, $^{13}C$ and $^{19}F$) confirmed that the product complied with the structure here below:

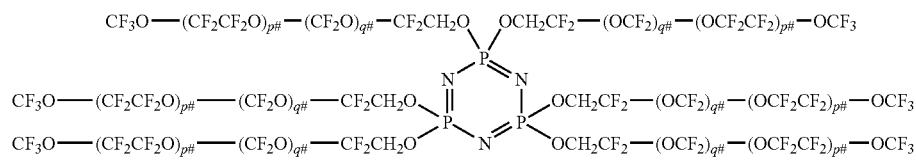

wherein $p^{\#}$ and $q^{\#}$ have the meaning above detailed.

EXAMPLE 2

Synthesis of a Pentasubstituted Phosphazene Comprising a Polar Group 7 g of the hexasubstituted phosphazene prepared as described in example 1 here above were introduced in a glass reactor equipped with mechanical stirrer, thermometer and a reflux condenser, together with 3.3 g of an aqueous 40% wt KOH solution and 3.2 g of ethanol. The mixture was allowed to react at 60-80° C. under vigorous stirring.

Hydrolysis reaction was followed by $^{31}P$-NMR. After 8 hours, the reaction was completed. The reaction mixture was then allowed to cool to room temperature and the two immiscible phases thus formed were separated. The heavy fluorinated phase was collected and separated from solvents residues by fractional distillation under reduced pressure.

5.25 g (purity: 95%) of a product complying with formula:

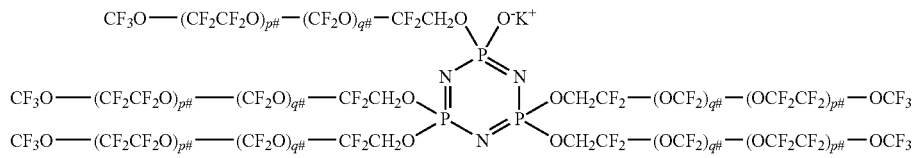

were obtained.

EXAMPLES 3 TO 6

Four Balls Wear Machine Testing

The phosphazenes of Examples 1 and 2 were added to perfluoropolyether lubricating oils either as such or in admixture and the so obtained compositions, as well as the neat lubricating oil taken as reference, were evaluated for their anti-wear properties. The anti-wear properties were evaluated according to the ASTM D 4172 standard.

Thus, three AISI N. E-52100 steel spheres, having a diameter of 12.7 mm, 25 EP (Extra Polish) degree, previously cleaned by washing by immersion in n-hexane (15 min) and subsequently in GALDEN® TM HT55 (for 15 minutes) and then dried, were introduced in a container equipped with a suitable cavity so as to have three points in contact and, then, they were coated with the lubricant compositions to be tested.

A fourth sphere having same features and submitted to analogous pre-treatment, was connected to an electric engine effecting its rotation, and placed on the three mentioned spheres with a load of 40+/−0.2 kgf (392N). The whole was assembled, closed and heated to 75°+/−2° C. Once said temperature reached, the fourth sphere, placed over the three of reference, was made to rotate at a rate of 1200+/−60 rpm for 60+/−1 minutes. At the end of the test the container was disassembled, the lubricant compositions were removed and the wear of the three spheres contained therein was evaluated by optical microscopy having a precision of 0.01 mm. The wear value expressed in mm, was obtained as arithmetic mean of six readings, measuring for each sphere, without removing it from the cavity, the wear diameter in the rotation direction and the diameter perpendicular to the first diameter.

Results are summarized in Table 1 here below.

EXAMPLE 7

Synthesis of a Pentasubstituted Phosphazene Comprising a Polar Group (Divalent Cation)

25 g of the pentasubstituted phosphazene prepared as described in example 2 here above were introduced in a glass reactor equipped with mechanical stirrer, thermometer and a reflux condenser, together with 3.35 g of an aqueous 12% wt HCl solution and 3.5 g of methanol. The mixture was allowed to react for 1 hour at 80° C. under vigorous stirring.

The reaction mixture was then allowed to cool to room temperature and the two immiscible phases thus formed were separated. The heavy fluorinated phase was collected, washed twice with methanol (2×10 g) and finally separated from solvents residues by fractional distillation under reduced pressure. The resulting product complying with formula:

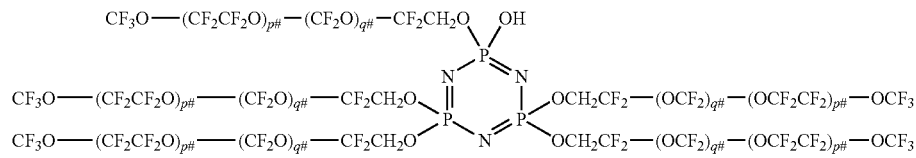

was introduced in a glass reactor equipped with mechanical stirrer together with 0.46 g of Ca(OH)$_2$, 250 ml of water, 250 g of methanol and 400 g of GALDEN® HT110. After 30 minutes of vigorous stirring at room temperature the two immiscible phases thus formed were separated. The heavy fluorinated phase was collected and finally separated from solvents residues by fractional distillation under reduced pressure. 24 g (purity: 95%) of a product complying with formula:

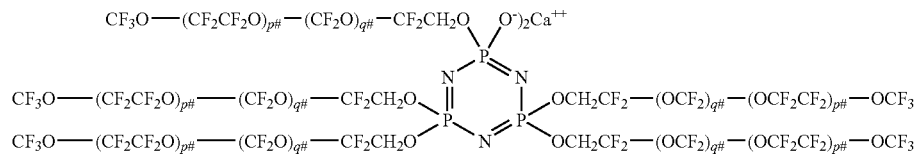

were obtained.

EXAMPLE 8

Four Balls Wear Machine Testing

The phosphazene of Example 7 was added to a perfluoropolyether lubricating oil and the mixture thereof was evaluated for its anti-wear properties following procedure described in examples 3 to 6. Data are summarized in table 1 here below.

TABLE 1

| Run | Lubricant | Anti-wear additive[1] | Test result |
|---|---|---|---|
| Ex. 3 (Comp.) | FOMBLIN ® YR1800 | none | 1.41 mm |
| Ex. 4 (Comp.) | FOMBLIN ® YR1800 | 3% wt of A | 1.15 mm |
| Ex. 5 | FOMBLIN ® YR1800 | 3% wt of B | 0.65 mm |
| Ex. 6 | FOMBLIN ® YR1800 | 3% wt of a mixture of 85% wt A and 15% wt B | 0.70 mm |
| Ex. 8 | FOMBLIN ® YR1800 | 3% wt of C | 0.58 cm |

[1]A is intended to denote the hexasubstituted phosphazene of example 1; B is intended to denote the pentasubstituted phosphazene of example 2 comprising a polar group; C is intended to denote the pentasubstituted phosphazene of example 3.

FOMBLIN® YR1800 is a lubricant having the following structure: $CF_3O(C_3F_6O)_n (CF_2O)_m CF_3$ wherein n/m= 20, having a number averaged molecular weight of roughly 7250 and a kinematic viscosity (ASTM D445) at 20° C. of 1850 cSt.

Data summarized in table 1 here above clearly demonstrate that the cyclic phosphazene compounds of the invention comprising a polar group have superior anti-wear properties when used as additives in perfluoropolyether lubricants; moreover, when used in combination with persubstituted phosphazenes of the prior art, thanks to the better dispersibility of the mixture, they can also substantially enhance the anti-wear properties of said additive composition.

The invention claimed is:

1. A cyclic phosphazene compound complying with formula (I) or (II):

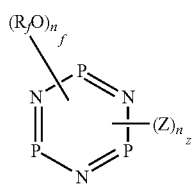
(I)

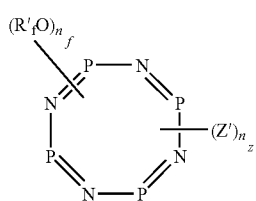
(II)

wherein:
$R_f$ and $R'_f$, equal to or different from each other and at each occurrence, represent independently, a (per)fluoropolyoxyalkylene chain [chain (OF)] comprising recurring units $R°$, said recurring units, distributed randomly through the (per)fluoropolyoxyalkylene chain, being chosen among:
(i) —CFXO—, wherein X is F or $CF_3$,
(ii) —$CF_2$CFXO—, wherein X is F or $CF_3$,
(iii) —$CF_2CF_2CF_2O$—,
(iv) —$CF_2CF_2CF_2CF_2O$—
Z and Z', equal to or different from each other and at each occurrence, represent a polar group of formula —O$^-$M$^+$, wherein M is chosen among hydrogen, a monovalent metal, an ammonium radical of formula $NR_1R_2R_3R_4$, wherein each of $R_1$, $R_2$, $R_3$, $R_4$ is, independently, an hydrogen atom or a $C_1$-$C_{12}$hydrocarbon group, optionally fluorinated, or a polar group of formula —O$^-$)$_2$M'$^{2+}$, wherein M' is a divalent metal [group (P)];
$n_z$ is an integer from 1 to 3
$n_{z'}$ is an integer from 1 to 4;
$n_f$ is an integer such that $n_z+n_f$ is equal to 8; and
$n_f$ is an integer such that $n_{z'}+n_f$ is equal to 6.

2. The cyclic phosphazene compound of claim 1, wherein the groups $R_fO$— and $R'_fO$— are selected from the group consisting of:

(a)

wherein:
J is a group of formula —CE'(Y)CE$_2$O(CH$_2$CH$_2$O)$_{s1}$- or —CE'YO(CH$_2$CH$_2$O)$_{s2}$-, wherein s1 and s2, equal to or different from each other and at each occurrence, are integers from 0 to 5, wherein Y is F or $CF_3$ and wherein E and E', equal to or different from each other and at each occurrence, are selected among F, H and $CF_3$;
T is selected from the group consisting of —$CF_3$, —$CF_2CF_3$, —$CF_2CF_2CF_3$, —(CF$_2$)$_f$—CF$_2$(T$_1$), and —(CF$_2$)$_f$—CF(T$_1$)(T$_2$), wherein f is 0 or 1, wherein T$_1$ and T$_2$, equal to or different from each other, are at each occurrence independently chosen among Cl, Br and H;
p' and q' are numbers such that p'+q' is in the range 1-100, and the q'/p' ratio is between 0.1 and 10;

(b)

wherein:
J has the same meaning as above described;
T' is selected from the group consisting of —$CF_3$, —CFY—$CF_3$, —CF(Y)CF(Y)CF$_3$, —(CFY)$_f$—CFY (T'$_1$), and —(CFY)$_f$—CY(T'$_1$) (T'$_2$), wherein f is 0 or 1, wherein T'$_1$ and T'$_2$, equal to or different from each other, are at each occurrence independently chosen among Cl, Br and H;
Y is F or $CF_3$;
r', s' and t' are numbers such that r'+s'+t' is in the range 1-100, and the t'/(r'+s') ratio is between 0.01 and 0.1;

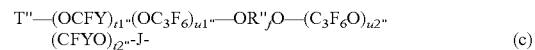
(c)

wherein:
J has the same meaning as above described;
R"$_f$ is a $C_1$-$C_8$ perfluoroalkylene;
Y is F or $CF_3$;
T" is selected from the group consisting of —$CF_3$, —CFY—$CF_3$, —CF(Y)CF(Y)CF$_3$, —(CFY)$_1$—CFY (T"$_1$), and —(CFY)$_f$—CY(T"$_1$)(T"$_2$), wherein f is 0 or 1, wherein T"$_1$ and T"$_2$, equal to or different from each other, are at each occurrence independently chosen among Cl, Br and H;
t1", u1", t2", u2" are numbers such that (t1"+u1"+t2"+u2") is in the range 1-100, and the (tl"+t2")/(u1"+u2") is between 0.01 and 0.1;

(d)

wherein:
J has the same meaning as above described;
T'" is selected from the group consisting of —$CF_3$, —$CF_2CF_3$, —$CF_2CF_2CF_3$, —(CF$_2$)$_f$—CF$_2$(T'"$_1$), and —(CF$_2$)$_f$—CF(T'"$_1$)(T'"$_2$), wherein f is 0 or 1, wherein T'"$_1$ and T'"$_2$, equal to or different from each other, are at each occurrence independently chosen among Cl, Br and H;

v' is a number in the range 1-100, and x' is 1 or 2; and

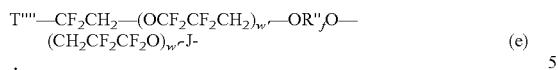
(e)

wherein:
J has the same meaning as above described;
$R''_f$ is as above;
T'''' is selected from the group consisting of —$CF_3$, —$CF_2CF_3$, —$CF_2CF_2CF_3$, —$(CF_2)_f$—$CF_2(T''''_1)$, and —$(CF_2)_f$—$CF(T''''_1)(T''''_2)$, wherein f is 0 or 1, wherein $T''''_1$ and $T''''_2$, equal to or different from each other, are at each occurrence independently chosen among Cl, Br and H;
w' is a number in the range 1-100.

3. The cyclic phosphazene compound of claim 2 complying with formula (III) or (IV):

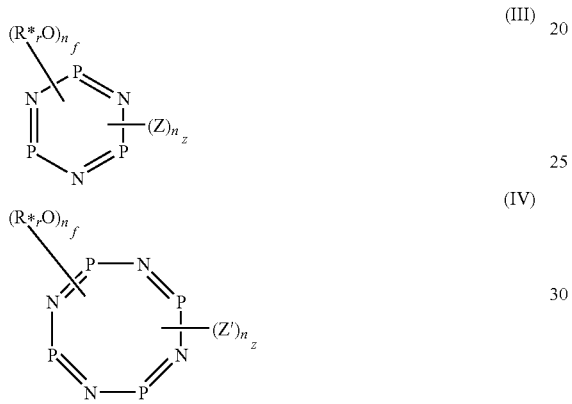
(III)
(IV)

wherein:
Z, Z', $n_z$, $n_z'$, $n_f'$, $n_f$ have the same meaning as above defined;
$R*_fO$— and $R*'_fO$— groups, equal to or different from each other and at each occurrence, represent independently, a (per)fluoropolyoxyalkylene chain of formula:

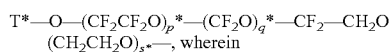

s* in a number from 0 to 5;
T* is selected from the group consisting of —$CF_3$, —$CF_2CF_3$, and —$CF_2CF_2CF_3$; and
p* and q* are numbers such that p*+q* is in the range 1-50, and the q*/p* ratio is between 0.1 and 10.

4. The cyclic phosphazene compound of claim 3, complying with formula (V) or (V-bis):

wherein:
M and M' have the same meaning as above defined; and
each of p*i (i=1 to 5) and q*i (i=1 to 5) is independently an integer ≧0 such that p*i+q*i is in the range 2-25, and the q*i/p*i ratio is between 0.1 and 10.

5. A process for preparing the cyclic phosphazene according to claim 1, said process comprising:
(i) reaction, in the presence of a base, of a perhalophosphazene of formula (VI) or (VII):

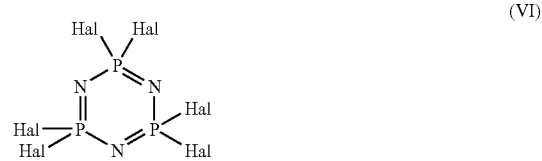
(VI)

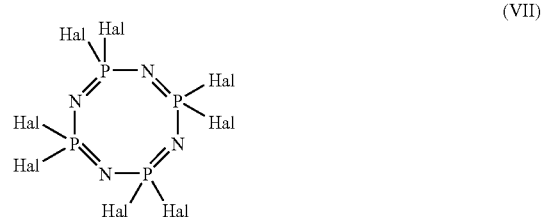
(VII)

wherein Hal represents an halogen selected from the group consisting of fluorine, chlorine, bromine, and iodine, with a fluorinated alcohol of formula $R_fOH$, wherein $R_f$ has the meaning as above detailed to convert the P-Hal moieties in P—$OR_f$ moieties; and
(ii) selective hydrolysis of at least one of the —P—$OR_f$ moieties per molecule to yield a —P—Z moiety, wherein Z has the meaning as above described.

6. A composition comprising the cyclic phosphazene compound according to claim 1.

7. The composition according to claim 6, said composition comprising another cyclic phosphazene compound free from polar group of type Z and Z' as above described (phosphazene (NP)).

8. The composition according to claim 7, said composition comprising a phosphazene (NP) complying with formula (VIII) to (X):

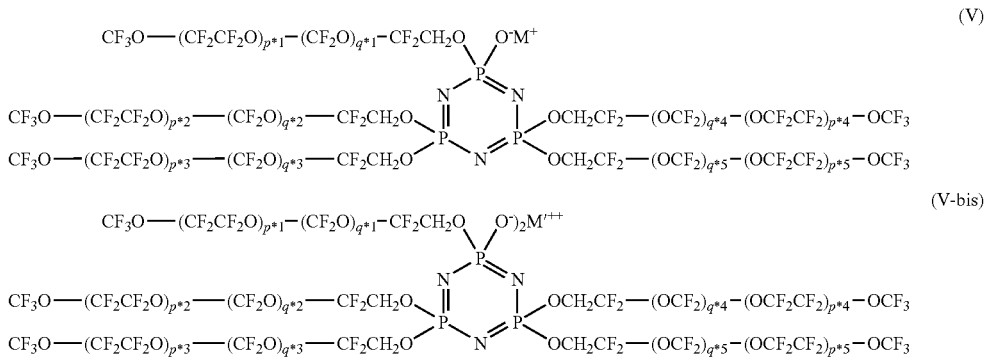
(V)
(V-bis)

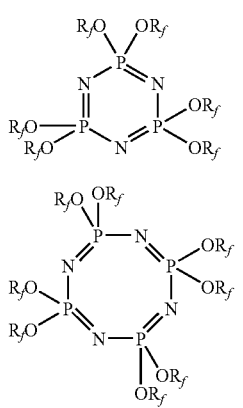

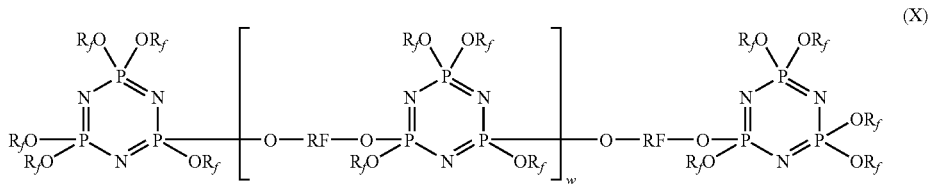

wherein $R_f$ has the meaning as above defined, wherein w is an integer equal to 0 or 1, wherein RF is a divalent group comprising recurring units $R°$, said recurring units, distributed randomly, being selected from the group consisting of:
(i) —CFXO—, wherein X is F or $CF_3$,
(ii) —$CF_2$CFXO—, wherein X is F or $CF_3$,
(iii) —$CF_2CF_2CF_2O$—, and
(iv) —$CF_2CF_2CF_2CF_2O$—.

9. The composition according to claim 6, said composition comprising a lubricant comprising at least one oil selected from the following groups consisting of:

$$B—O—[CF(CF_3)CF_2O]_{b1'}(CFXO)_{b2'}—B' \quad (1)$$

wherein:
X is equal to —F or —$CF_3$;
B and B', equal to or different from each other, are selected from the group consisting of —$CF_3$, —$C_2F_5$ and —$C_3F_7$;
b1' and b2', equal to or different from each other, are independently integers $\geq 0$ selected such that the b1'/b2' ratio is between 20 and 1,000, and b1'+b2' is in the range 5 to 250;

$$C_3F_7O—[CF(CF_3)CF_2O]_{o'}-D \quad (2)$$

wherein
D is equal to —$C_2F_5$ or —$C_3F_7$;
o' is an integer from 5 to 250;

$$\{C_3F_7O—[CF(CF_3)CF_2O]_{dd'}—CF(CF_3)—\}_2 \quad (3)$$

wherein
dd' is an integer between 2 and 250;

$$C'—O—[CF(CF_3)CF_2O]_{c1'}(C_2F_4O)_{c2'}(CFX)_{c3'}—C'' \quad (4)$$

wherein
X is equal to —F or —$CF_3$;
C' and C'', equal to or different from each other, are selected from the group consisting of —$CF_3$, —$C_2F_5$ and —$C_3F_7$, c1', c2' and c3' equal to or different from each other, are independently integers $\geq 0$, such that and c1'+c2'+c3' is in the range 5 to 250;

$$D—O—(C_2F_4O)_{d1'}(CF_2O)_{d2'}-D' \quad (5)$$

wherein
D and D', equal to or different from each other, are selected from the group consisting of —$CF_3$, —$C_2F_5$ and —$C_3F_7$;
d1' and d2' equal to or different from each other, are independently integers $\geq 0$, such that the d1'/d2' ratio is between 0.1 and 5, and d1'+d2' is in the range 5 to 250;

$$G-O—(CF_2CF_2C(Hal')_2O)_{g1'}—(CF_2CF_2CH_2O)_{g2'}—(CF_2CF_2CH(Hal')O)_{g3'}-G' \quad (6)$$

wherein
G and G', equal to or different from each other, are selected from the group consisting of —$CF_3$, —$C_2F_5$ and —$C_3F_7$;
Hal', equal to or different at each occurrence, is a halogen chosen among F and Cl;
g1', g2', and g3' equal to or different from each other, are independently integers $\geq 0$, such that g1'+g2'+g3' is in the range 5 to 250;

$$L-O—(CF_2CF_2O)_{l'}-L' \quad (7)$$

wherein
L and L', equal to or different from each other, are selected from the group consisting of —$C_2F_5$ and —$C_3F_7$;
l' is an integer in the range 5 to 250; and $$R^1_f—\{C(CF_3)_2—O—[C(R^2_f)_2]_{kk1'}C(R^2_f)_2—O\}_{kk2'}—R^1_f \quad (8)$$

wherein
$R^1_f$ is a perfluoroalkyl group having from 1 to 6 carbon atoms;
$R^2_f$ is equal to —F or perfluoroalkyl group having from 1 to 6 carbon atoms;
kk1' is an integer from 1 to 2;
kk2' represents a number in the range 5 to 250.

10. A method of improving anti-wear properties in a lubricant, comprising adding the cyclic phosphazene compound according to claim 1 to a lubricant.

11. The cyclic phosphazene compound of claim 1, wherein M is an alkaline metal selected from the group consisting of Li, Na, K and wherein M' is an alkaline earth metal selected from consisting of Ca and Mg.

12. The cyclic phosphazene compound of claim 1, wherein $n_z$ is equal to 1 and wherein $n_z'$ is equal to 1.

13. The cyclic phosphazene compound of claim 4, wherein M is an alkaline metal selected from the group consisting of Li, Na, and K, and wherein M' is an alkaline earth metal selected from the group consisting of Ca and Mg.

14. The process of claim 5, wherein Hal is chlorine.

15. A composition comprising the cyclic phosphazene compound prepared according to the process of claim 5, said composition further comprising another cyclic phosphazene compound free from polar group of type Z and Z' as above described (phosphazene (NP)).

* * * * *